United States Patent
Hong

(10) Patent No.: US 10,711,009 B2
(45) Date of Patent: Jul. 14, 2020

(54) METHOD OF PREPARING D-GLUCARO-1,4:6,3-DILACTONE

(71) Applicants: Hyundai Motor Company, Seoul (KR); Kia Motors Corporation, Seoul (KR)

(72) Inventor: Chae Hwan Hong, Seoul (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 0 days.

(21) Appl. No.: 16/213,461

(22) Filed: Dec. 7, 2018

(65) Prior Publication Data
US 2020/0062774 A1 Feb. 27, 2020

(30) Foreign Application Priority Data

Aug. 24, 2018 (KR) .................. 10-2018-0098934

(51) Int. Cl.
*C07D 493/04* (2006.01)
*B01J 39/20* (2006.01)

(52) U.S. Cl.
CPC ............ *C07D 493/04* (2013.01); *B01J 39/20* (2013.01)

(58) Field of Classification Search
CPC ................................ C07D 493/04; B01J 39/20
USPC ......................................................... 549/306
See application file for complete search history.

(56) References Cited

U.S. PATENT DOCUMENTS

| 5,312,967 A * | 5/1994 | Kiely | .................... C07C 69/675 549/305 |
| 6,049,004 A * | 4/2000 | Kiely | ...................... C07C 51/27 562/523 |
| 9,227,904 B1 * | 1/2016 | Hong | .................... C07C 51/313 |

OTHER PUBLICATIONS

Brown; Journal of Carbohydrate Chemistry, 2007, 26 455-467. (Year: 2007).*

(Continued)

*Primary Examiner* — Daniel R Carcanague
(74) *Attorney, Agent, or Firm* — Mintz Levin Cohn Ferris Glovsky and Popeo, P.C.; Peter F. Corless

(57) ABSTRACT

Disclosed is a method of preparing d-glucaro-1,4:6,3-dilactone using an organic acid or a salt thereof, such that d-glucaro-1,4:6,3-dilactone having high purity can be obtained using potassium glucarate as the organic acid, and simultaneously, the economic efficiency of the preparation process can be remarkably improved.

9 Claims, 3 Drawing Sheets

(56) References Cited

OTHER PUBLICATIONS

Dow Chemical, Publication 177-01509-904, "DOWEX™ Fine Mesh Spherical Ion Exchange Resins", Dated Oct. 25, 2008. Downloaded Jun. 14, 2019 from http://msdssearch.dow.com/Published-LiteratureDOWCOM/dh_006f/0901b8038006f232.pdf (Year: 2008).*
Hashimoto; J. Polym. Sci.: Part A Polym. Chem. 1993, 31, 3141-3149. (Year: 1993).*
Hashimoto; Makromol. Chem. Rapid Commun. 1990, 11, 393-396. (Year: 1990).*
Rohm and Haas, Product Data Sheet, PDS 0433 A, "AMBERLITE™ IR120H", Dated Jan. 2008. Downloaded Jun. 17, 2019 from https://nshosting.dow.com/doc-archive/business/ier/ier_for_industrial_water_treatment/amberlite_ir120_h/tds/annberlite_ir120_h.pdf (Year: 2008).*
Troy C. Gehret et al., Convenient Large-Scale Synthesis of D-Glucaro-1, 4:6, 3-dilactone, J. Org. Chem. 2009, 74, 8373-8376.
Troy C. Gehret et al., Convenient Large-Scale Synthesis of D-Glucaro-1, 4:6, 3 dilactone, Central Research & Development, E.I. DuPont de Nemours & Co., Experimental Stallion, Wilmington, Delaware 19880, 5 pages, 2009.

* cited by examiner

METHOD OF PREPARING D-GLUCARO-1,4:6,3-DILACTONE

CROSS-REFERENCE TO RELATED APPLICATION

This application claims under 35 U.S.C. § 119(a) the benefit of priority to Korean Patent Application No. 10-2018-0098934 filed on Aug. 24, 2018, the entire contents of which are incorporated herein by reference.

TECHNICAL FIELD

The present invention relates to a method of preparing d-glucaro-1,4:6,3-dilactone using an organic acid or a salt thereof.

BACKGROUND OF THE INVENTION

In the related arts, a method of preparing d-glucaro-1,4:6,3-dilactone using calcium D-glucarate as a starting material has been suggested. For instance, calcium ions can be separated from a calcium D-glucarate aqueous solution using an expensive ion exchange resin, which is followed by distillation using a solvent such as methyl isobutyl ketone (MIBK). However, the preparation of calcium D-glucarate may cost highly due to complicated process such as material separation and purification in order to increase the purity of the final product. In addition, the expensive ion exchange resin may not be sufficiently reused after recovery, undesirably increasing industrial preparation costs, because calcium salt in the aqueous solution and the oxidation of glucose have to be carried out simultaneously, which reactions do not occur efficiently.

Therefore, it is necessary to develop preparation techniques that are effective and easy and are industrially useful, compared to the aforementioned method.

SUMMARY OF THE INVENTION

In preferred aspects, the present invention may provide a novel method of preparing d-glucaro-1,4:6,3-dilactone. In particular, the method may include simplified process from complicated conventionally used process, thereby improving purity of a final product and the economic efficiency of the preparation process.

In one aspect, provided is a method of preparing d-glucaro-1,4:6,3-dilactone. The method may include: preparing an admixture including an organic acid or a salt thereof and a solvent component; contacting the admixture with an ion exchange resin; separating the ion exchange resin from the admixture; preparing a composition including 1,4-dioxane and the admixture from which the ion exchange resin has been separate. Preferably, the method may further include freezing and drying the composition to prepare particles of the d-glucaro-1,4:6,3-dilactone. Preferably, the solvent component may include a polar solvent such as water. In particularly, the solvent component may include water, or be water.

The term "organic acid" as used herein refers to an organic compound having acidic property, for example, by containing one or more functional group that can be ionized in water or an aqueous solution. Exemplary organic acid may suitably include carboxyl group (—COOH), sulfonic acids (e.g., —SO$_2$OH), alcohols (—OH) or thiol (—SH). Preferred organic acid may suitably include one or more carboxyl group, which may be ionized to produce —COO$^-$ end. In certain embodiments, the organic acid containing ionized group (e.g., —COO$^-$) may be in a "salt" form together with a cation such as a metal ion (e.g., Na$^+$, K$^+$, Ca$^{2+}$ or Mg$^{2+}$) or ammonium ion (NH$_4^+$).

The organic acid or the salt thereof may suitably include one or more potassium ions (K$^+$).

The organic acid may include potassium glucarate.

The admixture may include an amount of about 20 wt % to 40 wt % of the organic acid or the salt thereof based on the total weight of the admixture.

Preferably, the ion exchange resin may include a cation exchange resin. The cation exchange resin may suitably include a strongly acidic cation exchange resin.

The "strongly acidic cation exchange resin" as used herein refers to a resin material including a pendant group of sulfonic acid group (—SO$_3$H) such that the acidity thereof may be greater an acidity of hydrochloric acid or sulfuric acid. Preferably, the cation exchange resin may suitably include sulfonic acid group (—SO$_3$H).

The cation exchange resin may suitably include one or more selected from the group consisting of styrene, acrylic acid, phenol, epoxy, vinyl pyridine, and urea formaldehyde.

The cation exchange resin may suitably include a copolymer of styrene and divinylbenzene.

The organic acid or the salt thereof and the ion exchange resin may be incubated at a mass ratio of about 1:1 to 1:4.

The ion exchange resin and the admixture may be incubated for about 8 hr to 12 hr.

The composition may include the admixture from which the ion exchange resin has been separated and the 1,4-dioxane at a volume ratio of about 1:1 to 1:1.5.

The composition mixed solution may be frozen and dried at a temperature of about −70° C. or less for about 12 hr to 20 hr.

In another aspect, provided is a material comprising d-glucaro-1,4:6,3-dilactone prepared by the method described herein.

Further provided is an article comprising the material as described herein. Still further provided is a vehicle part comprising the article described herein.

According to various exemplary embodiments of the present invention, the method of preparing d-glucaro-1,4:6,3-dilactone from potassium glucarate may produce a final product having high purity and the economic efficiency of the preparation process may be improved.

DETAILED DESCRIPTION

Figure 1:
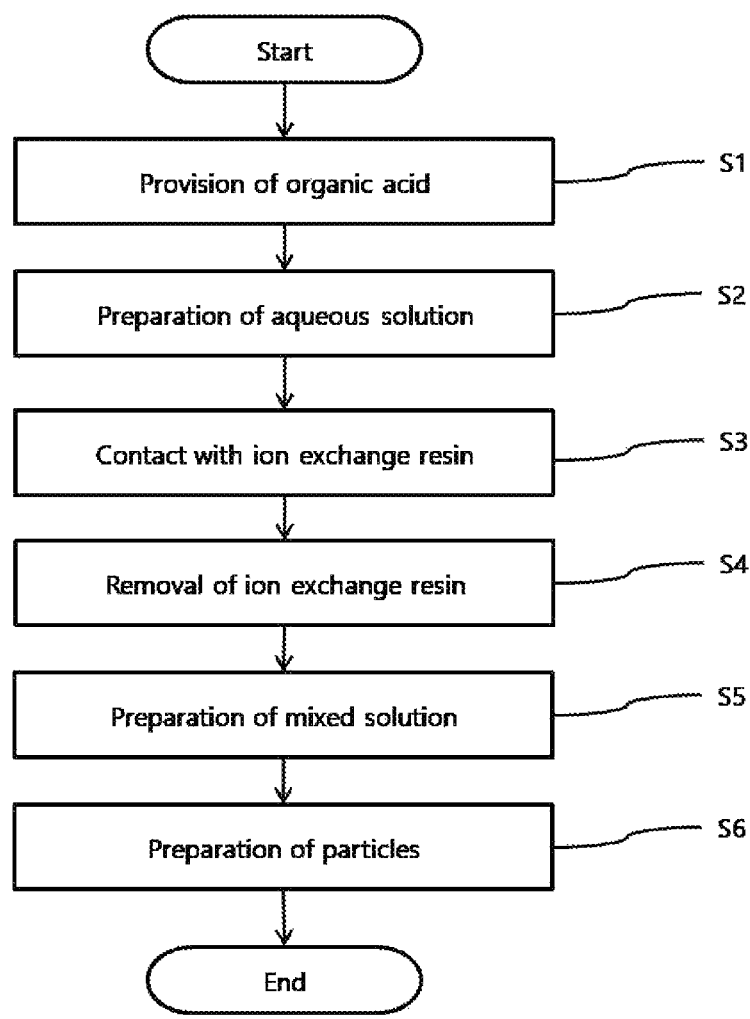
FIG. 1 shows an exemplary process of preparing d-glucaro-1,4:6,3-dilactone from an organic acid or a salt thereof according to an exemplary embodiment of the present invention.

The above and other aspects, features and advantages of the present invention will be more clearly understood from the following preferred embodiments taken in conjunction with the accompanying drawings. However, the present invention is not limited to the embodiments disclosed herein, and may be modified into different forms. These embodiments are provided to thoroughly explain the invention and to sufficiently transfer the spirit of the present invention to those skilled in the art.

Throughout the drawings, the same reference numerals will refer to the same or like elements. For the sake of clarity of the present invention, the dimensions of structures are depicted as being larger than the actual sizes thereof. It will be understood that, although terms such as "first", "second", etc. may be used herein to describe various elements, these elements are not to be limited by these terms. These terms are only used to distinguish one element from another element. For instance, a "first" element discussed below could be termed a "second" element without departing from the scope of the present invention. Similarly, the "second" element could also be termed a "first" element. As used herein, the singular forms are intended to include the plural forms as well, unless the context clearly indicates otherwise.

It will be further understood that the terms "comprise", "include", "have", etc., when used in this specification, specify the presence of stated features, integers, steps, operations, elements, components, or combinations thereof, but do not preclude the presence or addition of one or more other features, integers, steps, operations, elements, components, or combinations thereof. Also, it will be understood that when an element such as a layer, film, area, or sheet is referred to as being "on" another element, it can be directly on the other element, or intervening elements may be present therebetween. In contrast, when an element such as a layer, film, area, or sheet is referred to as being "under" another element, it can be directly under the other element, or intervening elements may be present therebetween.

Unless otherwise specified, all numbers, values, and/or representations that express the amounts of components, reaction conditions, polymer compositions, and mixtures used herein are to be taken as approximations including various uncertainties affecting the measurements that essentially occur in obtaining these values, among others, and thus should be understood to be modified by the term "about" in all cases. Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Furthermore, when a numerical range is disclosed in this specification, the range is continuous, and includes all values from the minimum value of said range to the maximum value thereof, unless otherwise indicated. Moreover, when such a range pertains to integer values, all integers including the minimum value to the maximum value are included, unless otherwise indicated.

In the present specification, when a range is described for a variable, it will be understood that the variable includes all values including the end points described within the stated range. For example, the range of "5 to 10" will be understood to include any subranges, such as 6 to 10, 7 to 10, 6 to 9, 7 to 9, and the like, as well as individual values of 5, 6, 7, 8, 9 and 10, and will also be understood to include any value between valid integers within the stated range, such as 5.5, 6.5, 7.5, 5.5 to 8.5, 6.5 to 9, and the like. Also, for example, the range of "10% to 30%" will be understood to include any subranges, such as 10% to 15%, 12% to 18%, 20% to 30%, etc., as well as all integers including values of 10%, 11%, 12%, 13% and the like up to 30%, and will also be understood to include any value between valid integers within the stated range, such as 10.5%, 15.5%, 25.5%, and the like.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, plug-in hybrid electric vehicles, hydrogen-powered vehicles and other alternative fuel vehicles (e.g. fuels derived from resources other than petroleum). As referred to herein, a hybrid vehicle is a vehicle that has two or more sources of power, for example both gasoline-powered and electric-powered vehicles.

In one aspect, provided is a novel preparation method to obtain d-glucaro-1,4:6,3-dilactone, and particularly to a method of preparing d-glucaro-1,4:6,3-dilactone using an organic acid.

Hereinafter, a detailed description will be given of the present invention.

A method of preparing d-glucaro-1,4:6,3-dilactone may include preparing an admixture including an organic acid or a salt thereof and a solvent component, for example, by mixing the organic acid to the solvent component; contacting (e.g., incubating) the admixture with the ion exchange resin; separating the ion exchange resin from the admixture; preparing a composition including 1,4-dioxane and the admixture from which the ion exchange resin has been separated; and preparing particles by freezing and drying the mixed solution.

FIG. 1 is a flowchart showing the steps of an exemplary process of preparing d-glucaro-1,4:6,3-dilactone. With reference thereto, the preparation method is described below.

Provision of Organic Acid (S1)

In the present invention, the organic acid or a salt thereof may be provided in a form including one or more potassium ions ($K^+$) bound to one or both ends thereof. Preferably, the organic acid may be potassium glucarate, for example, in a form in which potassium ($K^+$) is bound to an end thereof.

The potassium glucarate may be obtained by adding glucose serving as a starting material, potassium hydroxide (KOH) and a noble metal catalyst to a solvent, followed by an oxidation reaction.

The noble metal catalyst may include one or more metal elements selected from the group consisting of platinum, rhodium, palladium, and nickel, and the metal component may be loaded on a support including one or more selected from the group consisting of carbon, silica, and alumina.

In the present invention, the solvent may suitably include water.

Figure 2:
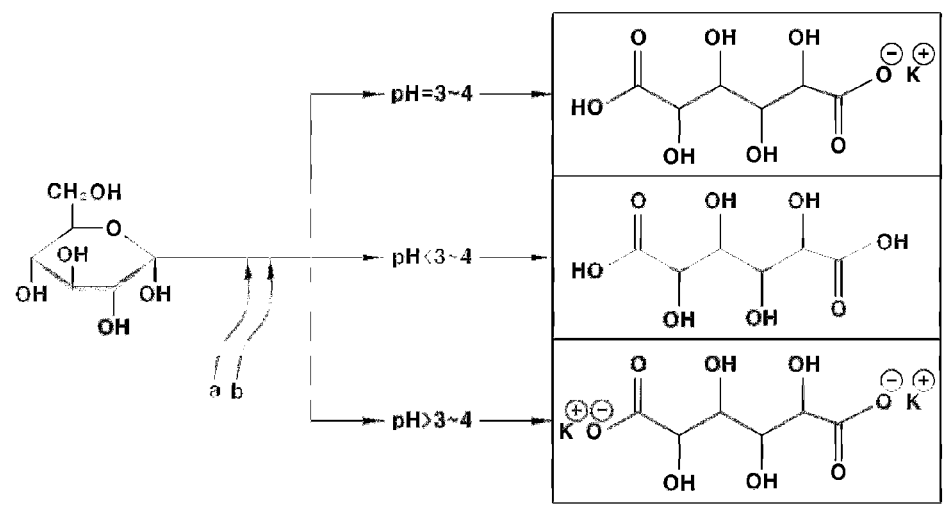
FIG. 2 shows an exemplary process of synthesizing an organic acid or a salt thereof from glucose according to an exemplary embodiment of the present invention.

FIG. 2 shows an exemplary process of converting a hexose monosaccharide, such as glucose, into the organic acid or the salt thereof, through catalytic oxidation. For instance, glucose, having a hexagonal shape, may be added to a polar solvent (e.g., water), together with potassium hydroxide (KOH) (a) and a noble metal catalyst (b) in the presence of oxygen gas, after which an oxidation reaction is induced, thus obtaining the organic acid or the salt thereof. The type of organic acid or the salt thereof may vary depending on the hydrogen ion concentration of the reaction conditions. For example, at a pH of about 3 to 4, glucaric acid in which a potassium cation ($K^+$) is present in the form of a salt at only one end thereof may be obtained. When the pH is less than 3, glucaric acid in which a potassium cation ($K^+$) is not present in the form of a salt may be obtained. When the pH is greater than 4, glucaric acid in which a potassium cation (K⁺) is present in the form of a salt at both ends thereof may be obtained. Preferably, the organic acid or the salt thereof may include, or be glucaric acid (potassium glucarate), in which a potassium cation (K⁺) is present in the form of a salt at only one end thereof.

Preparation of Admixture (S2)

Preferably, the admixture may suitably include an amount of about 20 wt % to 40 wt % of potassium glucarate, as the organic acid, based on the total weight of the admixture. The admixture may suitably prepared by adding the potassium glucarate to water and mixing the same, thus preparing the admixture.

Contact with Ion Exchange Resin (S3)

The admixture prepared in the previous step (S2) may be added and incubated with an ion exchange resin, and thus the organic acid or the salt thereof may be subjected to ion exchange through contact with the ion exchange resin.

Preferably, the ion exchange resin may be a cation exchange resin. The potassium ion of the organic acid may be exchanged with hydrogen ion by means of the added ion exchange resin.

Preferably, the cation exchange resin may suitably include a strongly acidic cation exchange resin. For instance, the cation exchange resin may include a sulfonic acid group (—SO₃H) as an exchange group.

The cation exchange resin may include one or more selected from the group consisting of styrene, acrylic acid, phenol, epoxy, vinyl pyridine, and urea formaldehyde. For instance, the cation exchange resin may include a copolymer of styrene and divinylbenzene.

A mass ratio of the organic acid and the ion exchange resin may be about 1:1 to 1:4. When the mass ratio is less than about 1:1, the purity of d-glucaro-1,4:6,3-dilactone, which is the final product, may be remarkably decreased. When the mass ratio is greater than about 1:4, the final product may contain large amounts of byproducts.

The ion exchange resin and the organic acid or the salt thereof may be brought into contact, or incubated with each other for about 8 hr to 12 hr.

Removal of Ion Exchange Resin (S4)

After ion exchange through sufficient contact between the organic acid or the salt thereof and the ion exchange resin in the previous step (S3), the ion exchange resin may be removed from the admixture through filtering.

The filtering may be performed using a filter paper, but the present invention is not limited thereto, and any process may be conducted, so long as it is able to completely remove or separate the ion exchange resin from the aqueous solution.

Preparation of Mixed Solution (S5)

The admixture remaining after removal of the ion exchange resin in the previous step (S4) may be added with 1,4-dioxane (99.8%) and mixed, thus preparing a composition.

1,4-dioxane is a dioxane, which may include an isomer of 1,2-dioxane and 1,3-dioxane. For example, 1,4-dioxane is a material having specific ether properties in which each oxygen has a functional group such that 1,4-dioxane is more polar than diethyl ether having the same number of carbon atoms. The boiling point thereof is 101° C., which is similar to that of water, and the freezing point thereof is 11.8° C. It has very high miscibility with water. Accordingly, even when some water is present during the reaction in the previous step, 1,4-dioxane may be very efficiently mixed therewith. Since the freezing point thereof is higher than that of water, water and 1,4-dioxane may be relatively easily separated from each other through a freezing process.

For example, 1,4-dioxane may be a solvent having very high polarity, and facilitate the formation of a ring structure of the glucaric acid ion from which the K⁺ ion has been separated, obtained in the previous step.

In the present invention, the volume ratio of the aqueous solution from which the ion exchange resin has been removed and the 1,4-dioxane may be of about 1:1 to 1:1.5. When the volume ratio is less than about 1:1, d-glucaro-1,4:6,3-dilactone, which is the final product, may not be efficiently prepared. When the volume ratio is greater than about 1:1.5, the final product may contain large amounts of impurities.

In the present invention, the mixing may be preferably performed for about 2 hr to 5 hr, for example, stirring.

Preparation of Particles (S6)

The mixed solution mixed with 1,4-dioxane in the previous step (S5) may be frozen using a cryogenic freezer and then dried using a freeze dryer, thus preparing particles.

The composition may be preferably frozen using the freezer at a temperature of about −70° C. or less for about 12 hr to 20 hr.

A better understanding of the present invention will be given through the following examples, which are merely set forth to illustrate the present invention but are not to be construed as limiting the scope of the present invention.

PREPARATION EXAMPLE

Preparation of Potassium Glucarate as Starting Material

As a starting material, glucose (hydrous glucose, Daesang, Korea) was placed at a concentration of 0.1 g/cc relative to water, serving as a solvent, in a reactor, and potassium hydroxide (Sigma Aldrich, USA) was added in an amount of 0.9 parts by weight based on the amount of glucose. Thereafter, a platinum catalyst (Sigma Aldrich, USA) loaded on activated carbon was added in an amount of 0.3 parts by weight based on the amount of glucose. Thereafter, the reactor temperature was maintained at a temperature of 50° C., and oxygen gas was fed into the reactor such that the pressure was maintained at about 1 bar, and the reaction was allowed to progress for 4 hr. Here, the hydrogen ion concentration was maintained at a pH of 4.

After completion of the reaction, potassium glucarate, which is an organic acid in a form in which potassium (K⁺) is bound to the end thereof, was obtained.

Figure 3:
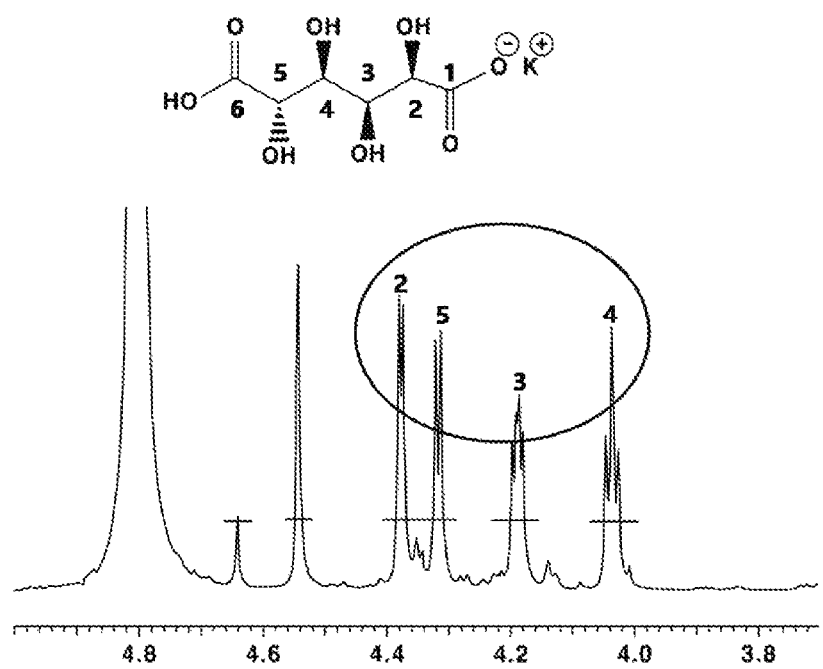
FIG. 3 is a $^1$H-NMR graph of prepared potassium glucarate.

FIG. 3 shows ¹H-NMR data of glucaric acid. In the ¹H-NMR graph, the peak at 4.39 on the X-axis represents the 2-position hydrogen of potassium glucarate, the peak at 4.32 represents the 5-position hydrogen of potassium glucarate, the peak at 4.19 represents the 3-position hydrogen of potassium glucarate, and the peak at 4.03 represents the 4-position hydrogen of potassium glucarate. Based on the ¹H-NMR graph showing the peaks at the above four positions, potassium glucarate, which is an organic acid in a form in which potassium K⁺) is bound to one end thereof, can be found to be synthesized.

EXAMPLES

Example 1

20 g of potassium glucarate obtained in the above Preparation Example was dissolved in 100 cc of water to give an aqueous solution, after which 40 g of an ion exchange resin (Amberlite® IR120 hydrogen form, Sigma Aldrich) was added to the aqueous solution, followed by contact treatment for 10 hr, and ion exchange resin particles were then removed through filtering using a filter paper.

The aqueous solution remaining after removal of the ion exchange resin particles was added with 100 cc of 1,4-dioxane (anhydrous, 99.8%, $C_4H_8O_2$, Sigma Aldrich) and mixed with stirring for 3 hr. After sufficient stirring, the solution was frozen at −70° C. using a cryogenic freezer and then dried for 12 hr using a freeze dryer, after which particles were obtained. The particles thus obtained were subjected to NMR (Nuclear Magnetic Resonance) to analyze the chemical structure of a desired product, from which whether a desired product was obtained was confirmed.

Examples 2 to 5

Particles were prepared in the same manner as in Example 1 under the respective conditions of Examples 2 to 5 shown in Table 1 below. The particles thus obtained were subjected to NMR (Nuclear Magnetic Resonance) to analyze the chemical structure of a desired product, whereby whether a desired product was produced was confirmed.

TABLE 1

| Composition | | Example 2 | Example 3 | Example 4 | Example 5 |
|---|---|---|---|---|---|
| Potassium glucarate (g) | | 22 | 24 | 25 | 25 |
| Ion exchange resin (g) | Amberlite ® IR120 hydrogen form | 45 | 43 | 50 | 55 |
| Solvent treatment agent ($cm^3$) | 1,4-dioxane | 105 | 110 | 115 | 120 |
| Drying type | Freeze drying | −70° C., 14 hr | −70° C., 16 hr | −70° C., 18 hr | −70° C., 20 hr |
| Solvent ($cm^3$) | Water | 95 | 105 | 102 | 103 |

Comparative Examples 1 to 7

Particles were prepared in the same manner as in Example 1 using the components in the amounts shown in Table 2 below. The particles thus obtained were subjected to NMR (Nuclear Magnetic Resonance) to analyze the chemical structure of a desired product, whereby whether a desired product was produced was confirmed.

TABLE 2

| Composition | | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|---|
| Potassium glucarate (g) | | 20 | 20 | 20 | 20 | 20 | 20 | 20 |
| Ion exchange resin (g) | Amberlite ® IR120 hydrogen form | | 40 | 40 | 40 | 40 | 40 | 10 |
| | Amberlite ® IRA400 chloride form | 40 | | | | | | |
| Solvent treatment agent (cc) | 1,4-dioxane | 100 | 100 | | | 100 | 50 | 100 |
| | Hexane | | | 100 | | | | |
| | MIBK | | | | 100 | | | |
| Drying type | Freeze drying | −70° C., 12 hr | −20° C., 12 hr | −70° C., 12 hr | −70° C., 12 hr | | −70° C., 12 hr | −70° C., 12 hr |
| | Rotary evaporation | | | | | 60° C., 5 hr | | |
| Solvent (cc) | Water | 100 | 100 | 100 | 100 | 100 | 100 | 100 |

Test Examples

The particles prepared in Examples 1 to 5 and Comparative Examples 1 to 7 were subjected to NMR to analyze the chemical structures thereof. The results of production of the final product, namely d-glucaro-1,4:6,3-dilactone, are summarized in Table 3 below.

TABLE 3

| | Example | | | | | Comparative Example | | | | | | |
|---|---|---|---|---|---|---|---|---|---|---|---|---|
| Item | 1 | 2 | 3 | 4 | 5 | 1 | 2 | 3 | 4 | 5 | 6 | 7 |
| d-glucaro-1,4:6,3-dilacton | O | O | O | O | O | X | X | X | X | X | X | X |

As is apparent from the test results, d-glucaro-1,4:6,3-dilactone was produced as the final product in Examples 1 to 5.

Figure 4:
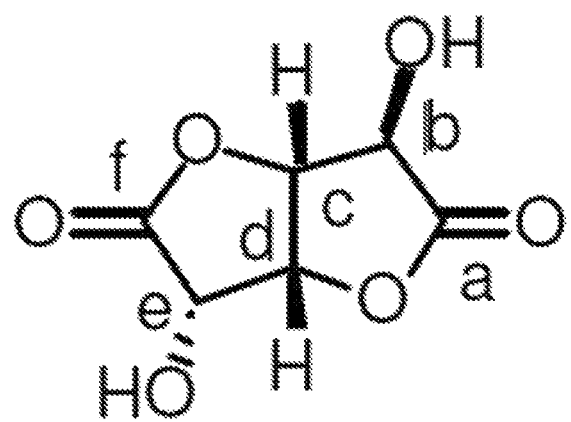
FIG. 4 is a chemical structure of prepared d-glucaro-1,4:6,3-dilactone.

FIG. 4 shows the chemical structure of the production of d-glucaro-1,4:6,3-dilactone The NMR results for the above chemical structures are as follows:

Respective peaks of the graph are summarized as follows.

$^1$H NMR (500 MHz, solvent: DMSO)

6.9 (br s, 1H, OHb)

6.5 (br d, J=5.2 Hz, 1H, OHe)

5.2 (dd, J=3.6, 4.0 Hz, 1JCH=170.2 Hz, 1H, Hd)

4.9 (d, J=3.6 Hz, 1JCH=168.4 Hz, 1H, Hc)

4.7 (d, J=4.0 Hz, 1JCH=144.5 Hz, 1H, He)

4.2 (s, 1JCH=156.5 Hz, 1H, Hb)

Thereby, d-glucaro-1,4:6,3-dilactone was confirmed to be produced.

In Comparative Examples 1 to 7, the above peaks were not observed, indicating that d-glucaro-1,4:6,3-dilactone was not obtained.

Although various exemplary embodiments of the present invention have been described with reference to the accompanying drawings, those skilled in the art will appreciate that the present invention may be embodied in other specific forms without changing the technical spirit or essential features thereof. Thus, the embodiments described above should be understood to be non-limiting and illustrative in every way.

What is claimed is:

1. A method of preparing d-glucaro-1,4:6,3-dilactone, comprising:
    preparing an admixture comprising an organic acid or a salt thereof and a solvent component, wherein the organic acid is prepared by adding glucose, potassium hydroxide (KOH) and noble metal catalyst to a solvent and reacting an oxidation;
    contacting the admixture with an ion exchange resin;
    separating the ion exchange resin from the admixture;
    preparing a composition comprising 1,4-dioxane and the admixture from which the ion exchange resin has been separated, and
    freezing and drying the composition to prepare particles of the d-glucaro-1,4:6,3-dilactone,
    wherein the admixture comprises an amount of about 20 wt % to 40 wt % of the organic acid or the salt thereof based on the total weight of the admixture,
    wherein the oxidation reaction proceeds at a pH of about 3 to 4,
    wherein the organic acid comprises a glucaric acid in which a potassium cation (K+) is present in the form of a salt at only one end,
    wherein the composition is frozen and dried at a temperature of about −70° C. or less for about 12 hr to 20 hr.

2. The method of claim 1, wherein the solvent component comprises water.

3. The method of claim 1, wherein the ion exchange resin comprises a cation exchange resin.

4. The method of claim 3, wherein the cation exchange resin comprises a sulfonic acid group (—SO$_3$H).

5. The method of claim 3, wherein the cation exchange resin comprises one or more selected from the group consisting of styrene, acrylic acid, phenol, epoxy, vinyl pyridine, and urea formaldehyde.

6. The method of claim 3, wherein the cation exchange resin comprises a copolymer of styrene and divinylbenzene.

7. The method of claim 1, wherein the organic acid or the salt thereof and the ion exchange are incubated at a mass ratio of about 1:1 to 1:4.

8. The method of claim 1, the ion exchange resin and the admixture are incubated for about 8 hr to 12 hr.

9. The method of claim 1, wherein the composition comprises the admixture from which the ion exchange resin has been removed and the 1,4-dioxane at a volume ratio of about 1:1 to 1:1.5.

* * * * *